US012031106B2

(12) United States Patent
Hölscher et al.

(10) Patent No.: US 12,031,106 B2
(45) Date of Patent: Jul. 9, 2024

(54) USE OF 1-ETHYL-4,4-DIMETHYL-CYCLOHEXANE DERIVATIVES AS FRAGRANCES

(71) Applicant: SYMRISE AG, Holzminden (DE)

(72) Inventors: Bernd Hölscher, Halle (DE); Vijayanand Chandrasekaran, Holzminden (DE)

(73) Assignee: SYMRISE AG, Holzminden (DE)

( * ) Notice: Subject to any disclaimer, the term of this patent is extended or adjusted under 35 U.S.C. 154(b) by 129 days.

(21) Appl. No.: 17/292,821

(22) PCT Filed: Nov. 12, 2018

(86) PCT No.: PCT/EP2018/080899
§ 371 (c)(1),
(2) Date: May 11, 2021

(87) PCT Pub. No.: WO2020/098901
PCT Pub. Date: May 22, 2020

(65) Prior Publication Data
US 2021/0395640 A1    Dec. 23, 2021

(51) Int. Cl.
*C11B 9/00* (2006.01)
*C07C 29/147* (2006.01)
*C07C 35/08* (2006.01)
*C07C 69/00* (2006.01)
*C07C 269/00* (2006.01)

(52) U.S. Cl.
CPC .......... *C11B 9/0034* (2013.01); *C07C 29/147* (2013.01); *C07C 35/08* (2013.01); *C07C 269/00* (2013.01); *C07C 2601/14* (2017.05)

(58) Field of Classification Search
CPC .................................................... C11B 9/0034
See application file for complete search history.

(56) References Cited

U.S. PATENT DOCUMENTS

| 4,187,251 | A | 2/1980 | Schleppnik |
| 2005/0182273 | A1* | 8/2005 | Eh .......................... C07C 69/675 560/259 |

FOREIGN PATENT DOCUMENTS

| DE | 1923223 A1 | 11/1969 |
| EP | 0868502 A1 | 10/1998 |
| WO | 1998013447 A1 | 4/1998 |

OTHER PUBLICATIONS

Takabe, et al. ("Cyclization of N,N-diethylgeranylamine N-oxide in one-pot operation: preparation of cyclic terpenoid-aroma chemicals", Tetrahedron Letters, (2008), 49(41) 6016-6018.) (Year: 2008).*
International Search Report and Written Opinion issued on Aug. 28, 2019 for corresponding PCT Application No. PCT/EP2018/080899.
International Search Report and Written Opinion issued on Feb. 21, 2020 for corresponding co-pending PCT Application No. PCT/EP2019/080968.
Normand Dufort et al., "Reduction de cetones conjuguees dans la serie acetyl methyl cyclohexene," Candian Journal of Chemistry, vol. 46, 1968, p. 1073 XP055612866.

* cited by examiner

*Primary Examiner* — Jessica Whiteley
(74) *Attorney, Agent, or Firm* — POLSINELLI PC

(57) ABSTRACT

The present invention relates to the use of 1-(4,4-dimethylcyclohexyl)ethanone, 1-(4,4-dimethylcyclohex-1-en-1-yl)ethanone, 1-(4,4-dimethylcyclohexyl)ethanol, 1-(4,4-dimethylcyclohexyl)ethyl acetate and 1-(2-hydroxy-4,4-dimethylcyclohexyl)ethanone as a fragrance substance, in particular with a flowery and/or fruity olfactory characteristic. The present invention further relates to fragrance compositions and perfumed products comprising the compounds listed above. The present invention also relates to a method producing perfumed products and a method producing 1-(4,4-dimethylcyclohexyl)ethanol or 1-(4,4-dimethylcyclohexyl)ethyl acetate. Further, the invention relates to the compounds 1-(4,4-dimethylcyclohexyl)ethyl acetate, 1-(4,4-dimethylcyclohexyl)ethanol and 1-(2-hydroxy-4,4-dimethylcyclohexyl)ethanone.

19 Claims, No Drawings

USE OF 1-ETHYL-4,4-DIMETHYL-CYCLOHEXANE DERIVATIVES AS FRAGRANCES

CROSS-REFERENCE TO RELATED APPLICATIONS

This application is a national stage application (under 35 U.S.C. § 371) of PCT/EP2018/080899, filed Nov. 12, 2018, which is incorporated herein by reference in its entirety.

The present invention relates primarily to the use of 1-(4,4-dimethylcyclohexyl)ethanone, 1-(4,4-dimethylcyclohex-1-en-1-yl)ethanone, 1-(4,4-dimethylcyclohexyl)ethanol, 1-(4,4-dimethylcyclohexyl)ethyl acetate and 1-(2-hydroxy-4,4-dimethylcyclohexyl)ethanone as fragrance substances, in particular with a flowery and/or fruity olfactory characteristic. The present invention further relates to fragrance compositions and perfumed products comprising the previously listed compounds. The present invention also relates to a method for the production of perfumed products and a process for the production of 1-(4,4-dimethylcyclohexyl)ethanol or 1-(4,4-dimethylcyclohexyl)ethyl acetate. Furthermore, the invention relates to the compounds 1-(4,4-dimethylcyclohexyl)ethyl acetate, 1-(4,4-dimethylcyclohexyl)ethanol and 1-(2-hydroxy-4,4-dimethylcyclohexyl)ethanone.

Further aspects and preferred embodiments of the present invention will be apparent from the following explanations, the examples and, in particular, the appended patent claims.

In the perfume industry, there is generally a need for new fragrance substances with flowery and/or fruity olfactory characteristics, since new and modern fragrances with flowery and/or fruity olfactory notes are to be continuously made available to consumers. Fragrances with flowery and/or fruity olfactory notes are used in large quantities and countless variations in fragrance compositions (perfume compositions) and perfumed products for a wide variety of applications. Due to the increasing consumer demand for new modern olfactory notes, there is a constant need in the fragrance industry for new fragrance substances that can be used in fragrance compositions to achieve novel effects and thus create new fashion trends. Compounds with flowery and/or fruity olfactory notes have always been important and sought-after components in the fragrance industry. Thus, today, fragrance substances with flowery and/or fruity olfactory notes are used in many fragrance compositions and are of great interest to the fragrance industry, especially if they have a rose or violet note.

Compounds with flowery and/or fruity olfactory notes are already known from the prior art, although the chemical structures of the compounds differ greatly. This is also consistent with the prevailing opinion that odor prediction is impossible based on chemical structure (e.g., Sell, C. S. (2006), Zur Unmöglichkeit der Geruchsvorhersage. Applied Chemistry, 118: 6402-6410). Thus, it is not possible to predict the odor of the compound based on a chemical structure, nor is it possible to "design" a chemical compound to a desired odor that merely needs to be synthesized in the laboratory and then necessarily exhibits that desired odor.

EP2474301A1 describes the use of cyclopent-2-enyl acetic acid ethyl ester in fragrance compositions. Cyclopent-2-enyl acetic acid ethyl ester exhibits a flowery olfactory note.

WO2018171865A1 describes the use of 5-bicyclo[2.2.1]hept-2-enyl acetate as a fragrance and/or flavor compound. 5-Bicyclo[2.2.1]hept-2-enyl acetate exhibits a woody, fruity and/or flowery odor.

In DE1923223A1, derivatives of 1-ethyl-3,3-dimethylcyclohexane, such as 1-(3,3-dimethylcyclohexyl)ethyl acetate, are described. The addition of 5% 1-(3,3-dimethylcyclohexyl)ethyl acetate to an odor composition can impart "warmth and a pleasant natural musk nuance" to the fragrance composition. The odor of 1-(3,3-dimethylcyclohexyl)ethyl acetate is stated to be "intense, flowery-woody."

DE102004047536A1 describes the use of 4-isoamylcyclohexanol as a flowery fragrance substance.

The search for suitable fragrances compounds with flowery and/or fruity olfactory characteristics, which led to the present invention, was impeded by the following facts:

The mechanisms of olfactory perception are not sufficiently known.

The connections between the specific olfactory perception on the one hand and the chemical structure of the associated fragrance substance on the other hand have not been sufficiently researched.

Often even minor changes in the structural set-up of a known fragrance substance cause major changes in the sensory properties and affect the tolerance for the human organism.

Not all compounds that have a (desired) odor are suitable for use as fragrance substances, for example because they are toxic or not sufficiently stable.

The success of the search for suitable fragrances with flowery and/or fruity olfactory characteristics therefore depends heavily on the intuition of the searcher.

It was the primary task of the present invention to identify compounds that can be used as fragrance substances, in particular fragrance substances with flowery and/or fruity olfactory characteristics. Such fragrances should preferably be suitable for scenting or perfuming certain products.

In this context, these fragrances should preferably meet one, several or preferably all of the following requirements:
easy accessibility,
strong effect in low concentrations,
largely or completely colorless
high stability in diverse mixtures or, respectively, preparations, wherein particularly no discoloration and/or separation and/or clouding shall occur.
inert behavior,
no toxic and/or allergic effect on humans, Furthermore, perfumed products as well as methods for the production of such products should be provided accordingly.

Furthermore, the present invention should particularly disclose new, advantageous fragrance compositions containing such fragrance substances.

The primary object of the present invention is solved by the use of a compound selected from the group comprising 1-(4,4-dimethylcyclohexyl)ethanone, 1-(4,4-dimethylcyclohex-1-en-1-yl)ethanone, 1-(4,4-dimethylcyclohexyl)ethanol, 1-(4,4-dimethylcyclohexyl)ethyl acetate and 1-(2-hydroxy-4,4-dimethylcyclohexyl)ethanone as a fragrance substance. Surprisingly, it has been shown that 1-(4,4-dimethylcyclohexyl)ethanone, 1-(4,4-dimethylcyclohex-1-en-1-yl)ethanone, 1-(4,4-dimethylcyclohexyl)ethanol, 1-(4,4-dimethylcyclohexyl)ethyl acetate and 1-(2-hydroxy-4,4-dimethylcyclohexyl)ethanone can be used as fragrance substance and, in particular, have a flowery and/or fruity olfactory characteristic. Surprisingly, own investigations have shown that these compounds are capable of imparting, enhancing or modifying a flowery and/or fruity olfactory note in accordance with the invention.

Additionally, it turned out surprisingly that the compounds used according to the invention are sufficiently stable and non-toxic.

Particularly preferred according to the invention is the use of 1-(4,4-dimethylcyclohexyl)ethyl acetate as a fragrance substance.

The compounds 1-(4,4-dimethylcyclohexyl)ethanone, 1-(4,4-dimethylcyclohex-1-en-1-yl)ethanone, 1-(4,4-dimethylcyclohexyl)ethanol, 1-(4,4-dimethylcyclohexyl)ethyl acetate and 1-(2-hydroxy-4,4-dimethylcyclohexyl)ethanone or the stereoisomers of these compounds described below are also referred to in this text as the compounds to be used according to the invention.

The compounds used according to the invention have the following general formula (I):

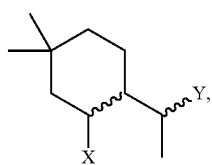

(I)

wherein X is hydrogen or hydroxy, Y is oxygen, hydroxy or acetate (in particular ethyl acetate), and the wavy bonds independently represent single bonds or double bonds. In the case of 1-(4,4-dimethylcyclohexyl)ethyl acetate, both wavy bonds are single bonds, X is hydrogen and Y is ethyl acetate. In the case of 1-(4,4-dimethylcyclohexyl)ethanol, X is hydrogen, both wavy bonds are single bonds, and X is hydroxy (OH). In the case of 1-(2-hydroxy-4,4-dimethylcyclohexyl)ethanone, X is hydroxy (OH), the wavy bond within the cyclohexyl is a single bond, Y is oxygen (O), and the wavy bond between Y and the carbon is a double bond. In the case of 1-(4,4-dimethylcyclohexyl)ethanone, X is hydrogen, the wavy bond within the cyclohexyl is a single bond, Y is oxygen (O), and the wavy bond between Y and the carbon is a double bond. In the case of 1-(4,4-dimethylcyclohex-1-en-1-yl)ethanone, X is hydrogen, Y is oxygen (O) and the two wavy bonds are double bonds. Thus, the compounds used in accordance with the invention share a common property or effect and all have a common chemical structure that constitutes a major part of their structure.

A further aspect of the present invention is the compound 1-(4,4-dimethylcyclohexyl)ethyl acetate. 1-(4,4-dimethylcyclohexyl)ethyl acetate has the following structure (A):

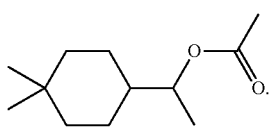

(A)

1-(4,4-Dimethylcyclohexyl)ethyl acetate exhibits a flowery olfactory characteristic, particularly of rose. In addition, the odor can be described as green, herbaflorate, violet and powdery. Due to a chiral center of the compound, the compound exists in two enantiomeric forms, which are shown below as compounds A1 and A2:

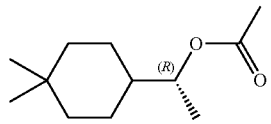

(A1)

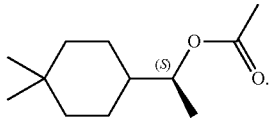

(A2)

Compound A1 is (R)-1-(4,4-dimethylcyclohexyl)ethyl acetate and compound A2 is (S)-1-(4,4-dimethylcyclohexyl)ethyl acetate. According to the invention, (R)-1-(4,4-dimethylcyclohexyl)ethyl acetate, (S)-1-(4,4-dimethylcyclohexyl)ethyl acetate or mixtures of both enantiomers are preferably racemic mixtures of both enantiomers. Possible mixing ratios between (R)-1-(4,4-dimethylcyclohexyl)ethyl acetate and (S)-1-(4,4-dimethylcyclohexyl)ethyl acetate are, for example, 1:9, 1:4, 3:7, 4:6, 1:1 (racemate), 6:4, 7:3, 4:1 and 9:1.

Another aspect of the present invention is the compound 1-(4,4-dimethylcyclohexyl)ethanol. 1-(4,4-Dimethylcyclohexyl)ethanol has the following structure (B):

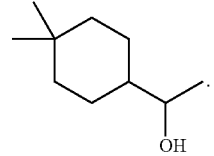

(B)

1-(4,4-Dimethylcyclohexyl)ethanol exhibits a flowery, blossoming, soft, creamy, citrus, plum olfactory characteristic. Due to a chiral center of the compound, the compound exists in two enantiomeric forms, which are shown below as compounds B1 and B2:

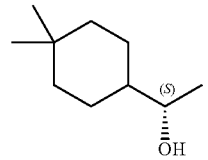

(B1)

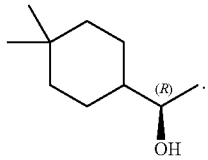

(B2)

Compound B1 is (S)-1-(4,4-dimethylcyclohexyl)ethanol and compound A2 is (R)-1-(4,4-dimethylcyclohexyl)ethanol. According to the invention, (R)-1-(4,4-dimethylcyclohexyl)ethanol, (S)-1-(4,4-dimethylcyclohexyl)ethanol or mixtures of both enantiomers, preferably racemic mixtures of both enantiomers. Possible mixture ratios between (R)-1-(4,4-dimethylcyclohexyl)ethanol and (S)-1-(4,4-dimethylcyclohexyl)ethanol are, for example, 1:9, 1:4, 3:7, 4:6, 1:1 (racemate), 6:4, 7:3, 4:1 and 9:1.

Another aspect of the present invention is the compound 1-(2-hydroxy-4,4-dimethylcyclohexyl)ethanone. 1-(2-Hydroxy-4,4-dimethylcyclohexyl)ethanone has the following structure (C):

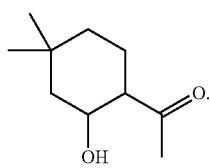
(C)

1-(2-Hydroxy-4,4-dimethylcyclohexyl)ethanone exhibits a slightly flowery, green and minty olfactory characteristic. Due to two chiral centers of the compound, the compound exists in four stereoisomeric forms, which are shown below as compounds C1 to C4:

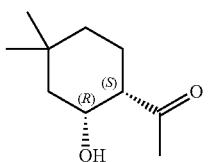
(C1)

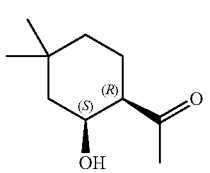
(C2)

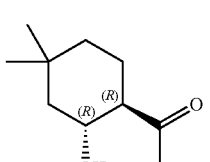
(C3)

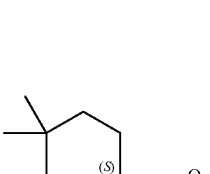
(C4)

Compound C1 is 1-((1S,2R)-2-hydroxy-4,4-dimethylcyclohexyl)ethanone, compound C2 is 1-((1R,2S)-2-hydroxy-4,4-dimethylcyclohexyl)ethanone, compound C3 is, 1-((1R,2R)-2-hydroxy-4,4-dimethylcyclohexyl)ethanone, and compound C4 is, 1-((1S,2S)-2-hydroxy-4,4-dimethylcyclohexyl)ethanone. According to the invention are 1-((1S,2S)-2-hydroxy-4,4-dimethylcyclohexyl)ethanone, 1-((1S,2R)-2-hydroxy-4,4-dimethylcyclohexyl)ethanone, 1-((1R,2S)-2-hydroxy-4,4-dimethylcyclohexyl)ethanone, 1-((1R,2R)-2-hydroxy-4,4-dimethylcyclohexyl)ethanone or mixtures thereof. 1-(4,4-Dimethylcyclohexyl)ethanone has the following structure (D):

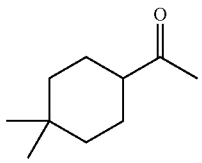
(D)

and exhibits a flowery, savory, caraway olfactory characteristic. 1-(4,4-Dimethylcyclohex-1-en-1-yl)ethanone has the following structure (E):

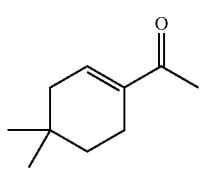
(E)

and exhibits a fruity, banana-like, caraway olfactory characteristic.

According to the invention, the stereoisomers of the compounds 1-(4,4-dimethylcyclohexyl)ethanol, 1-(4,4-dimethylcyclohexyl)ethyl acetate and 1-(2-hydroxy-4,4-dimethylcyclohexyl)ethanone described above may be used individually or as mixtures.

Another aspect of the present invention relates to fragrance compositions comprising a compound selected from the group comprising 1-(4,4-dimethylcyclohexyl)ethanone, 1-(4,4-dimethylcyclohex-1-en-1-yl)ethanone, 1-(4,4-dimethylcyclohexyl)ethanol, 1-(4,4-dimethylcyclohexyl)ethyl acetate and 1-(2-hydroxy-4,4-dimethylcyclohexyl)ethanone.

Preferred according to the invention is a fragrance composition additionally comprising one or more further fragrance substances.

Particularly preferred is or are the additional or one, more or all of the additional fragrance substances selected from the group consisting of alcohols, aldehydes, ketones, ethers, esters and carboxylates, preferably alcohols and aldehydes, in particular those having a molar mass in the range from 150 to 285 g/mol, preferably 210 g/mol or less. In context of the present invention, it generally applies that the fragrance substances additionally contained in a fragrance composition according to the invention have a molecular weight in the range from 150 to 285 g/mol, preferably from 210 g/mol or less. Particularly preferred fragrance substances to be used are described below.

Preferred according to the invention is a fragrance composition additionally comprising 1-(3,3-dimethylcyclohexyl)ethyl acetate.

Surprisingly, it was found that especially combinations of the compounds to be used according to the invention with 1-(3,3-dimethylcyclohexyl)ethyl acetate lead to fragrance compositions with excellent olfactory properties.

In this context, fragrance compositions are preferred according to the invention, wherein the molar ratio between the compound used according to the invention and 1-(3,3-dimethylcyclohexyl)ethyl acetate is 1:199 to 1:4, preferably 1:199 to 1:9, particularly preferably 2:99 to 1:19, more preferably 1:49 to 1:24.

Particularly in the molar ratios specified herein, particularly preferred olfactory properties of the fragrance compositions are exhibited.

Preferred according to the invention is a fragrance composition, wherein the compound used according to the invention is 1-(4,4-dimethylcyclohexyl)ethyl acetate.

Preferred according to the invention is a fragrance composition comprising 1-(4,4-dimethylcyclohexyl)ethyl acetate and one or more further fragrance substances.

Preferred according to the invention is a fragrance composition comprising 1-(4,4-dimethylcyclohexyl)ethyl acetate and 1-(3,3-dimethylcyclohexyl)ethyl acetate and optionally one or more further fragrance substances.

In this respect, fragrance compositions are preferred according to the invention, wherein the molar ratio between 1-(4,4-dimethylcyclohexyl)ethyl acetate and 1-(3,3-dimethylcyclohexyl)ethyl acetate is 1:199 to 1:4, preferably 1:199 to 1:9, particularly preferably 2:99 to 1:19, more preferably 1:49 to 1:24.

Examples of fragrance substances that can in principle be used advantageously as components of a fragrance composition according to the invention can be found, for example, in S. Arctander, Perfume and Flavor Chemicals, Vol. I and II, Montclair, N. J., 1969, self-published or H. Surburg, J. Panten, Common Fragrance and Flavor Materials, 5th Ed., Wiley-VCH, Wein-heim 2006.

The further fragrance substances used according to the invention may also be essential oils, concretes, absolues, resins, resinoids, balsams and/or tinctures. Preferred essential oils, concretes, absolues, resins, resinoids, balsams and/or tinctures that can be a component of an odorant mixture according to the invention are preferably selected from the group consisting of:

Ambergris tincture; Amyris oil; Angelica seed oil; Angelica root oil; Anise oil; Valerian oil; Basil oil; tree moss-Absolue; Bay oil; mugwort oil; Benzoe resin; Bergamot oil; Beeswax-Absolue; birch tar oil; bitter almond oil; savory oil; Bucco leaf oil; Cabreuva oil; Cade oil; Calmus oil; Camphor oil; Cananga oil; Cardamomen oil; Cascarilla oil; Cassia oil; Cassie-Absolue; Castoreum absolue; cedar leaf oil; cedar wood oil; Cistus oil; Citronella oil; lemon oil; Copaiva balm; Copaiva balm oil; Coriander oil; Costus root oil; Cumin oil; Cypress oil; Davana oil; dill weed oil; dill seed oil; Eau de brouts-Absolue; oakmoss-Absolue; Elemi oil; tarragon oil; Eucalyptus-citriodora-oil; Eucalyptus oil; Fennel oil; spruce needle oil; Galbanum oil; Galbanum resin; Geranium oil; Grapefruit oil; Guajac wood oil; Gurjun balm; Gurjun balm oil; Helichrysum-Absolue; Helichrysum oil; ginger oil; Iris root-Absolue; Iris root oil; Jasmine-Absolue; Calamus oil; Chamomile oil blue; Chamomile oil roman; carrot seed oil; Cascarilla oil; pine needle oil; spearmint oil; caraway seed oil; Labdanum oil; Labdanum-Absolue; Labdanum resin; Lavandin-Absolue; Lavandin oil; Lavender-Absolue; Lavender oil; Lemongras oil; lovage oil; Lime oil distilled; Lime oil pressed; Linaloe oil; Litsea-cubeba-oil; lorel leaf oil; Macis oil; Marjoram oil; Mandarin oil; Massoir bark oil; Mimosa-Absolue; musk corn oil; musk tincture; Muscatel-sage-oil; nutmeg oil; Myrrh-Absolue; Myrrh oil; Myrtle oil; carnation leaf oil; carnation blossom oil; Neroli oil; Olibanum-Absolue; Olibanum oil; Opopanax oil; Orange blossom-Absolue; Orange oil; Origanum oil; Palmarosa oil; Patchouli oil; Perilla oil; Peru balm oil; parsley leaf oil; parsley seed oil; Petitgrain oil; peppermint oil; Pepper oil; allspice oil; Pine oil; Poley oil; Rose-Absolue; rose wood oil; rose oil; rosemary oil; sage oil dalmatian; sage oil spanish; sandal wood oil; celery seed oil; spike lavender oil; star anise oil; Styrax oil; Tagetes oil; fir needle oil; tea tree oil; turpentine oil; thyme oil; tolu balm; tonka-Absolue; tuberose-Absolue; vanilla extract; violet-leaf-Absolue; verbena oil; vetiver oil; juniper berry oil; wine yeast oil; wormwood oil; wintergreen oil; ylang oil; hyssop oil; civet-Absolue; cinnamon leaf oil; cinnamon bark oil.

Preferred fragrance substances (individual fragrance substances) that are preferably used as part of a fragrance composition according to the invention, are selected from the group of hydrocarbons, preferably 3-carene; a-pinene; b-pinene; a-terpinene; g-terpinene; p-cymene; bisabolene; camphene; caryophyllene; cedrene; farnesene; limonene; longifolene; myrcene; ocimene; valencene; (E,Z)-1,3,5-undecatriene; styrene; diphenylmethane;

of aliphatic alcohols, preferably hexanol; octanol; 3-octanol; 2,6-dimethylheptanol; 2-methyl-2-heptanol; 2-methyl-2-octanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;

of aliphatic aldehydes and their acetals, preferably hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undecadienal; heptanaldiethyl acetal; 1,1-dimethoxy-2,2,5-trimethyl-4-hexene; citronellyloxy acetaldehyde; 1-(1-methoxy-propoxy)-(E/Z)-3-hexene;

of aliphatic ketones and their oximes, preferably 2-heptanone; 2-octanone; 3-octanone; 2-nonanone; 5-methyl-3-heptanone; 5-methyl-3-heptanonoxime; 2,4,4,7-tetramethyl-6-octen-3-one; 6-methyl-5-hepten-2-one;

of aliphatic sulfur-containing compounds, preferably 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthen-8-thiol;

of aliphatic nitriles, preferably 2-nonenoic acid nitrile; 2-undecenoic acid nitrile; 2-tridecenoic acid nitrile; 3,12-tridecadienoic acid nitrile; 3,7-dimethyl-2,6-octadienoic acid nitrile; 3,7-dimethyl-6-octenoic acid nitrile;

of esters of aliphatic carboxylic acids, preferably (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octene-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl 2-methyl pentanoate; ethyl hexanoate; allyl hexanoate; ethyl heptanoate; allyl heptanoate; Ethyl octanoate; Ethyl (E,Z)-2,4-decadienoate; Methyl 2-octinate; Methyl 2-noninate; Allyl 2-isoamyloxyacetate; Methyl 3,7-dimethyl-2,6-octadienoate; 4-methyl-2-pentyl crotonate;

of acyclic terpene alcohols, preferably citronellol; geraniol; nerol; linalool; lavadulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol 2,6-dimethyl-2,5,7-octatrien-1-ol; and their formates, acetates, propionates, isobutyrates, butyrates, isovalerianates, pentanoates, hexanoates, crotonates, tiglinates and 3-methyl-2-butenoates;

of acyclicterpene aldehydes and ketones, preferably geranial; neral; citronellal; 7-hydroxy-3,7-dimethyloctanal; 7-methoxy-3,7-dimethyloctanal; 2,6,10-trimethyl-9-undecenal; geranylacetone; and the dimethyl and diethylacetals of geranial, neral, 7-hydroxy-3,7-dimethyloctanal;

of cyclic terpene alcohols, preferably isopulegol; alpha-terpineol; terpinenol-4; menthan-8-ol; menthan-1-ol; menthan-7-ol; borneol; isoborneol; linalool oxide; nopol; cedrol; ambrinol; vetiverol; guaiacol; and their formates, acetates, propionates, isobutyrates, butyrates, isovalerianates, pentanoates, hexanoates, crotonates, tiglinates and 3-methyl-2-butenoates; menthyl formate; menthyl propionate; menthyl butyrate; menthyl isobutyrate; menthyl isovalerianate; menthyl hexanoate; menthyl crotonate; menthyl tetlinate;

of cyclic terpene aldehydes and ketones, preferably menthone; isomenthone; 8-mercaptomenthan-3-one; carvone; camphor; fenchone; alpha-ionone; beta-ionone; beta-n-methylionone; beta-isomethylionone; alpha-irone; alpha-damascone; beta-damascone; beta-damascenone; delta-damascone; gamma-damascone; 1-(2,4, 4-Trimethyl-2-cyclohexen-1-yl)-2-buten-1-one; 1,3,4, 6,7,8a-Hexahydro-1,1,5,5-tetramethyl-2H-2,4a-methanonaphthalen-8(5H)-one; 2-Methyl-4-(2,6,6-trimethyl-1-cyclohexen-1-yl)-2-butenal; Nootkatone; dihydroneootkatone; 4,6,8-megastigmatrien-3-one; alpha-sinensal; beta-sinensal; acetylated cedarwood oil (methylcedrylketone);

of cyclic alcohols, preferably 4-tert-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

of cycloaliphatic alcohols, preferably alpha, 3,3-trimethylcyclohexylmethanol; 1-(4-isopropylcyclohexyl)ethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

of cyclic and cycloaliphatic ethers, preferably cineole; cedryl methyl ether; cyclododecyl methyl ether; 1,1-dimethoxycyclododecane; (ethoxymethoxy)cyclododecane; alpha-cedrene epoxide; 3a,6,6,9a-tetramethyl-dodecahydronaphtho[2,1-b]furan; 3a-ethyl-6,6,9a-trimethyldodecahydronaphtho[2,1-b]furan; 1,5,9-trimethyl-13-oxabicyclo[10. 1.0]trideca-4,8-diene; rose oxide; 2-(2,4-dimethyl-3-cyclohexen-1-yl)-5-methyl-5-(1-methylpropyl)-1,3-dioxane;

of cyclic and macrocyclic ketones, preferably 4-tert-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5, 5-tetramethylcyclohexanone; 4-tert.-pentylcyclohexanone; 5-cyclohexadecen-1-one; 6,7-dihydro-1,1,2, 3,3-pentamethyl-4(5H)-indanone; 8-cyclohexadecen-1-one; 9-cycloheptadecen-1-one; cyclopentadecanone; cyclohexadecanone;

of cycloaliphatic aldehydes, preferably 2,4-dimethyl-3-cyclohexenecarbaldehyde; 2-methyl-4-(2,2,6-trimethyl-cyclohexen-1-yl)-2-butenal; 4-(4-hydroxy-4-methylpentyl)-3-cyclohexenecarbaldehyde; 4-(4-methyl-3-penten-1-yl)-3-cyclohexenecarbaldehyde;

of cycloaliphatic ketones, preferably 1-(3,3-dimethylcyclohexyl)-4-penten-1-one; 2,2-dimethyl-1-(2,4-dimethyl-3-cyclohexen-1-yl)-1-propanone; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl 2,6,10-trimethyl 2,5,9-cyclododecatrienyl ketone; tert.-butyl-(2,4-dimethyl-3-cyclohexen-1-yl)ketone;

of esters of cyclic alcohols, preferably 2-tert-butylcyclohexyl acetate; 4-tert-butylcyclohexyl acetate; 2-tert-pentylcyclohexyl acetate; 4-tert-pentylcyclohexyl acetate; 3,3,5-trimethylcyclohexyl acetate; decahydro-2-naphthyl acetate; 2-cyclopentylcyclopentyl crotonate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5, or 6-indenyl acetate; 4,7-methano-3a,4,5,6,7,7a-hexahydro-5, or 6-indenyl propionate; 4,7-methano-3a,4,5,6,7,7a-hexahydro-5, or 6-indenyl isobutyrate; 4,7-methanooctahydro-5, or 6-indenyl acetate;

of esters of cycloaliphatic alcohols, preferably 1-cyclohexylethyl crotonate;

of esters of cycloaliphatic carboxylic acids, preferably allyl 3-cyclohexyl propionate; allyl cyclohexyloxy acetate; cis- and trans-methyl dihydrojasmonate; cis- and trans-methyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate; ethyl-2-methyl-1,3-dioxolane-2-acetate;

of araliphatic alcohols, preferably benzyl alcohol; 1-phenylethyl alcohol; 2-phenylethyl alcohol; 3-phenyl propanol; 2-phenyl propanol; 2-phenoxyethanol; 2,2-dimethyl-3-phenyl propanol; 2,2-dimethyl-3-(3-methylphenyl) propanol; 1,1-dimethyl-2-phenylethyl alcohol; 1,1-dimethyl-3-phenylpropanol; 1-ethyl-1-methyl-3-phenylpropanol; 2-methyl-5-phenylpentan-1-ol; 3-methyl-5-phenylpentanol; 3-phenyl-2-propen-1-ol; 4-methoxybenzyl alcohol; 1-(4-isopropylphenyl) ethanol;

the esters of araliphatic alcohols and aliphatic carboxylic acids, preferably benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethyl benzyl acetate; alpha, alpha-dimethylphenylethyl acetate; alpha,alpha-dimethylphenylethyl butyrate; cinnamyl acetate; 2-phenoxyethyl isobutyrate; 4-methoxybenzyl acetate;

of araliphatic ethers, preferably 2-phenylethyl methyl ether; 2-phenylethyl isoamyl ether; 2-phenylethyl 1-ethoxyethyl ether; phenylacetaldehyde dimethyl acetal; phenylacetaldehyde diethyl acetal; hydratropaaldehyde dimethyl acetal; phenylacetaldehyde glycerol acetal; 2,4,6-trimethyl-4-phenyl-1,3-dioxane; 4,4a,5, 9b-tetrahydroindeno[1,2-d]-m-dioxin; 4,4a,5,9b-tetrahydro-2,4-dimethylindeno[1,2-d]-m-dioxin;

of aromatic and araliphatic aldehydes, preferably benzaldehyde; phenylacetaldehyde; 3-phenylpropanal; hydratropaaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-tert.-butylphenyl)propanal; 2-methyl-3-(4-isobutylphenyl)propanal; 3-(4-tert.-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

of aromatic and araliphatic ketones, preferably acetophenone; 4-methylacetophenone; 4-methoxyacetophenone; 4-tert.-butyl-2,6-dimethylacetophenone; 4-phenyl-2-butanone; 4-(4-hydroxyphenyl)-2-butanone; 1-(2-naphthalenyl)ethanone; 2-benzofuranylethanone; (3-methyl-2-benzofuranyl)ethanone; benzophenone; 1,1,2,3,3,6-hexamethyl-5-indanyl methyl ketone; 6-tert.-butyl-1,1-dimethyl-4-indanyl methyl ketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthone;

of aromatic and araliphatic carboxylic acids and their esters, preferably benzoic acid; phenylacetic acid; methyl benzoate; ethyl benzoate; hexyl benzoate; methyl phenyl acetate; ethyl phenyl acetate; geranyl phenyl acetate; phenyl ethyl phenyl acetate; methyl cinnamate; ethyl cinnamate; benzyl cinnamate; phenylethyl cinnamate; cinnamyl cinnamate; allyl phenoxy acetate; methyl salicylate; isoamyl salicylate; hexyl salicylate; cyclohexyl salicylate; cis-3-hexenyl salicylate; benzyl salicylate; phenyl ethyl salicylate; methyl-2,4-dihydroxy-3,6-dimethylbenzoate; ethyl-3-phenyl glycidate; ethyl-3-methyl-3-phenyl glycidate;

of nitrogen-containing aromatic compounds, preferably 2,4,6-trinitro-1,3-dimethyl-5-tert-butylbenzene; 3,5-dinitro-2,6-dimethyl-4-tert.-butylacetophenone; cinnamic acid nitrile; 3-methyl-5-phenyl-2-pentenoic acid nitrile; 3-methyl-5-phenylpentanoic acid nitrile; methyl anthranilate; methyl N-methyl anthranilate; Schiff bases of methyl anthranilate with 7-hydroxy-3,7-dimethyloctanal, 2-methyl-3-(4-tert.-butylphenyl)propanal or 2,4-dimethyl-3-cyclohexene carbaldehyde; 6-isopropylquinoline; 6-isobutylquinoline; 6-sec-butylquinoline; 2-(3-phenylpropyl)pyridine; indole; scatole; 2-methoxy-3-isopropylpyrazine; 2-isobutyl-3-methoxypyrazine;

of phenols, phenyl ethers and phenyl esters, preferably estragole; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenyl acetate;

of heterocyclic compounds, preferably 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

of lactones, preferably 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 4-methyl-1,4-decanolide; 1,15-pentadecanolide; cis- and trans-11-pentadecen-1,15-olide; cis- and trans-12-pentadecene-1,15-olide; 1,16-hexadecanolide; 9-hexadecene-1,16-olide; 10-oxa-1,16-hexadecanolide; 11-oxa-1,16-hexadecanolide; 12-oxa-1,16-hexadecanolide; ethylene-1,13-tridecanedioate; coumarin; 2,3-dihydrocoumarin; octahydrocoumarin.

Fragrance compositions according to the invention are typically liquid at 25° C. and 1013 hPa and are usually homogeneous solutions.

Fragrance compositions often comprise synthetic or natural (preferably) tasteless and odorless carrier oils, which contain the fragrance substances (as artificial or natural substances) in a highly concentrated form (as well as, optionally, perfumery solvents and/or excipients).

Perfume oils (as a preferred embodiment of fragrance compositions according to the invention) are frequently used for fragrance applications. Perfumes with perfume oils are produced, for example, by adding them to (e.g. alcoholic) solutions that, when evaporated, "entrain" the fragrance substances or odor substances and thus impart to the olfactory organ of the user, i.e. the human being, the sensory impression of a particular odor. Such mixtures can be, for example, a perfume, eau de parfum or eau de toilette. Furthermore, perfume oils serve to create a certain scent in living spaces, such as when used in fragrance lamps, nebulizers or diffusers. Perfume oils may further be applied in a variety of other products or compositions, for example, ranging from shoe polish to hair shampoos, sanitary towels to toilet cleaners, facial creams to washing powders and cat stones.

Another aspect of the present invention relates to perfumed products comprising a compound selected from the group comprising 1-(4,4-dimethylcyclohexyl)ethanone, 1-(4,4-dimethylcyclohex-1-en-1-yl)ethanone, 1-(4,4-dimethylcyclohexyl)ethanol, 1-(4,4-dimethylcyclohexyl)ethyl acetate and 1-(2-hydroxy-4,4-dimethylcyclohexyl)ethanone.

The compounds used according to the invention are thereby preferably present in a sensorially effective amount in the perfumed product.

"Sensorially effective amount" in the present context means that the perfumed product according to the invention allows the sensory characteristics of the fragrance composition according to the invention to be recognized during operation or use.

Preferred products are, for example, perfume extracts, eau de parfums, eau de toilettes, aftershaves, eau de colognes, pre-shave products, splash colognes and perfumed refreshing tissues, as well as perfumed acidic, alkaline and neutral cleaning agents or those to be perfumed, such as floor cleaners, window glass cleaners, dishwashing detergents, bathroom and sanitary cleaners, scouring agents, solid and liquid toilet cleaners, toilet sticks, toilet stones (liquid or solid), powdery and foamy carpet cleaners, liquid detergents, powder detergents, laundry pre-treatment agents such as bleaches, softeners and stain removers, fabric softeners, laundry soap, laundry tablets, disinfectants, surface disinfectants and air refreshers in liquid or gel-like form or mounted on a solid carrier, especially for deodorizing exhaust air from air-conditioning systems and industrial processes, as well as air refreshers in the form of aerosol or pump sprays, waxes and polishes such as furniture polishes, floor waxes, shoe polishes, strengthening, impregnating or deodorizing textile treatment products, diapers, sanitary towels, pant liners, plasters, as well as personal care products such as solid and liquid soaps, shower gels, shampoos, shaving soaps, shaving foams, bath oils, wet wipes, oil-in-water, water-in-oil and water-in-oil-in-water cosmetic emulsions such as Skin creams and lotions, facial creams and lotions, sunscreen creams and lotions, after-sun creams and lotions, hand creams and lotions, foot creams and lotions, depilatory creams and lotions, after-shave creams and lotions, tanning creams and lotions, hair care products, such as hair sprays, hair gels, strengthening hair lotions, hair conditioners, permanent and semi-permanent hair colorants, hair shaping products such as cold wave and hair straightening products, hair tonics, hair creams and lotions, deodorants and antiperspirants, e.g. underarm sprays, roll-ons, deodorant sticks, deodorant creams, decorative cosmetic products such as eye shadows, make-ups, lipsticks, mascara, as well as candles, lamp oils, incense sticks, animal litter, cat litter, insecticides, repellents, liquid and gaseous propellants, heating oils and heating gases.

Particularly preferred according to the invention is a perfumed product, wherein the product is selected from the group consisting of perfume extracts, eau de parfums, eau de toilettes, aftershaves, eau de colognes, pre-shave products, splash colognes, perfumed refreshing tissues, acidic, alkaline and neutral detergents, fabric refresher, ironing aids, liquid detergents, powder detergents, laundry pre-treatment agents, fabric softeners, laundry soaps, washing tablets, disinfectants, surface disinfectants, air refreshers, aerosol sprays, waxes and polishes, personal care products, hand creams and lotions, foot creams and lotions, depilatory creams and lotions, after-shave creams and lotions, tanning creams and lotions, hair care products, deodorants and antiperspirants, decorative cosmetic products, candles, lamp oils, incense sticks, insecticides, repellents and propellants.

Particularly preferred perfumed products according to the invention are selected from the following list:
  eau de parfums, eau de toilettes, after-shave, eau de colognes, pre-shave products, splash colognes;
  acidic, alkaline and neutral cleaning agents, especially in the household sector, preferably floor cleaners, window glass cleaners, dishwashing detergents, bathroom and sanitary cleaners, scouring agent, solid and liquid toilet cleaners, powder and foam carpet cleaners, liquid detergents, powder detergents, fabric softeners, surface disinfectants, especially for hard surfaces (hard surface cleaners);
  personal care products, preferably solid and liquid soaps, shower gels, shampoos, shaving soaps, shaving foams;
  cosmetic emulsions of the oil-in-water, water-in-oil and water-in-oil-in-water type, preferably skin creams and lotions, facial creams and lotions, sunscreen creams and lotions, after-sun creams and lotions, hand creams and lotions, foot creams and lotions, depilatory creams and lotions, after-shave creams and lotions, skin tanning creams and lotions, skin whitening creams and lotions;
  hair care products, preferably hair sprays, hair gels, setting hair lotions, hair conditioners, permanent and semi-permanent hair colorants, hairtonics, hair creams and lotions;
  deodorants and antiperspirants, preferably underarm sprays, roll-ons (preferably as alcoholic or non-alcoholic solution, as gel or (micro)emulsion, deodorant sticks, deodorant creams.

Particularly preferred perfumed products according to the invention are detergents and cleaning agents, hygiene or care products, especially in the field of body and hair care, cosmetics and household.

Preferred perfumed products according to the invention are also those in which the proportion of the fragrance composition according to the invention in the perfumed product is 0.01 to 10 wt.-%, preferably 0.1 to 5 wt.-%, particularly preferably 0.25 to 3 wt.-%, based on the total mass of the respective perfumed product.

A product according to the invention can also be based on a product to be odor-improved by reducing an unpleasant odor or by enhancing a pleasant olfactory impression (in particular as described herein).

According to a preferred embodiment, the compounds to be used according to the invention, or corresponding mixtures thereof, or fragrance compositions (as described herein) are adsorbed on a carrier, which ensures both fine distribution of the compounds in the product and controlled release during use. Such carriers may be porous inorganic materials such as silica gels, zeolites, gypsums, clays, clay granules, aerated concrete, etc., or organic materials such as woods and cellulose-based materials.

The compounds to be used according to the invention, or corresponding mixtures thereof or fragrance compositions (as described herein), may also be microencapsulated, spray-dried, be present as inclusion complexes or as extrusion products and added in this form to a product.

Optionally, the properties of such modified compounds to be used according to the invention or corresponding mixtures thereof or fragrance compositions (as described herein) can be further optimized by so-called "coating" with suitable materials with respect to a more targeted release, for which purpose waxy plastics such as polyvinyl alcohol are preferably used.

Microencapsulation of the compounds to be used according to the invention or corresponding mixtures thereof or fragrance compositions (as described herein) can be carried out, for example, by the so-called coacervation process with the aid of capsule materials, e.g. of polyurethane-like substances or soft gelatin. Spray-dried compounds to be used according to the invention can be prepared, for example, by spray-drying a substance to be used according to the invention or an emulsion or dispersion containing a corresponding mixture, wherein modified starches, proteins, dextrin and/or vegetable gums can be used as carriers. Inclusion complexes can be prepared, for example, by incorporating dispersions, which are compounds to be used according to the invention or corresponding mixtures thereof or comprise such, and cyclodextrins or urea derivatives in a suitable solvent, e.g. water. Extrusion products can be made by melting the compound(s) to be used according to the invention or corresponding mixtures thereof with a suitable waxy substance and by extrusion with subsequent solidification, optionally in a suitable solvent, e.g. isopropanol.

The compounds to be used according to the invention or corresponding mixtures thereof or fragrance compositions (as described herein) may be used in many preparations or products, preferably combined with one or more of the following excipients or active ingredients:

Preservatives, abrasives, anti-acne agents, anti-aging agents, antibacterial agents, anti-cellulitis agents, anti-dandruff agents, anti-inflammatory agents, anti-irritant agents, irritation inhibiting agents, antimicrobial agents, antioxidants, astringents, sweat inhibiting agents, antiseptics, antistatics, binders, buffers, carriers, chelating agents, cell stimulants, cleansing agents, caring agents, depilatories, surface-active agents, deodorizers, antiperspirants, plasticizers, emulsifiers, enzymes, essential oils, fibers, fixatives, foaming agents, foam stabilizers, anti-foaming agents, foam boosters, fungicides, gelling agents, gel-forming agents, hair care products, hair shaping products, hair straightening products, moisturizing products, moistening products, moisture retaining products, bleaching products, (textile) strengthening products, stain removing products, optical brightening products, impregnating agents, dirt-repellent agents, friction-reducing agents, lubricants, moisturizing creams, ointments, opacifiers, plasticizing agents, covering agents, polish, brighteners, polymers, powders, proteins, refatting agents, abrasive agents, silicones, skin soothing agents, skin cleansing agents, skin caring agents, skin healing agents, skin whitening agents, skin protecting agents, skin softening agents, cooling agents, skin cooling agents, warming agents, skin warming agents, stabilizers, UV absorbing agents, UV filters, detergents, fabric softeners, suspending agents, skin tanning agents, thickening agents, vitamins, oils, waxes, fats, phospholipids, saturated fatty acids, mono- or poly-unsaturated fatty acids, α-hydroxy acids, polyhydroxy fatty acids, liquefiers, dyes, color-protecting agents, pigments, anticorrosives, flavors, flavor substances, fragrance substances, polyols, surfactants, electrolytes, organic solvents, or silicones.

According to one embodiment of the present invention, a preferred product according to the invention, in particular a deodorant or the like, further contains (depending on the desired mode of action) one or more of the following active ingredients:

(1) Antimicrobially active substances which inhibit the development of the microorganisms responsible for perspiration odor; for example, triclosanâ (5-chloro-2-(2,4-dichlorophenoxy)phenol), triclocarban, chlorhexidine, chlorhexidine hydrochloride, chlorhexidine diacetate, chlorhexidine digluconate, 2-phenoxyethanol, farnesol, glycerol esters and ethers such as glycerol monolaurate, glycerol monocaprinate, hexoxyglycerol, octoxyglycerol (=ethylhexylglycerol, 3-(2-ethylhexyloxy-1,2-propanediol) or Sensiva® SC 50 (from Schülke & Mayr), aliphatic 1,2-diols such as 1,2-decanediol (EP 1 269 983), araliphatic alcohols such as described e.g. in EP 799 174, preferably 4-methyl-4-phenyl-2-pentanol (Vetikol; WO 03/024907) or 2-methyl-4-phenyl-2-butanol (1,1-dimethyl-3-phenyl-propanol, alpha, alpha-dimethylphenethylcarbinol), 1-menthylmethyl ether as described in WO 02/41861, 2-benzylheptan-1-ol (Jasmol; 2-n-pentyl-3-phenylpropan-1-ol), 2,2-dimethyl-3-phenylpropanol (muguet alcohol; cf. U.S. Pat. No. 4,091,090), antimicrobially active secondary alcohols, such as described e.g. in WO 2005/004601, in particular 3-methyl-6-phenyl-2-hexanol, 4-(2,4-dimethylphenyl)-2-butanol, 6-(4-isopropylphenyl)-3-methyl-2-hexanol, 4-(2,4,5-trimethylphenyl)-2-butanol, 3,3-dimethyl-4-phenyl-2-butanol, 3-methyl-4-(2-methylphenyl)-2-butanol, 6-(3,4-dimethylphenyl)-2-hexanol, aliphatic carboxylic acids such as 2-hexyloctanoic acid, 2-hexyldecanoic acid, 2-butyloctanoic acid or 2-butyldecanoic acid;

(2) enzyme-inhibiting substances that inhibit the action of enzymes involved in the formation of perspiration odor; for example, citric acid esters and metal-chelating substances such as EDTA (ethylenediaminetetraacetic acid), EGTA [ethylenebis(oxyethylenenitrilo)-tetraacetic acid] and DTPA (diethylenetriaminepentaacetic acid, pentetic acid);

(3) odor-absorbing substances that absorb substances responsible for perspiration odor; for example, zinc rizinoleate, cyclodextrins;

(4) antiperspirants, which inhibit sweat secretion and thus remove the breeding ground for the bacteria responsible for body odor. In general, astringent metal salts are preferably used as antiperspirants, especially inorganic and organic metal salts of the elements aluminum, zinc, magnesium, tin and zirconium and mixtures thereof, wherein halides such as aluminum chloride, basic aluminum hydroxychlorides, zirconyl oxychlorides and zirconyl hydroxychlorides and mixtures thereof are used in particular. Frequently, these aluminum and zirconium salts and mixtures thereof are also used in a complexed form, wherein propylene glycol, polyethylene glycol or glycine are preferably used as complexing agents.

As can be seen from the explanations above, compounds to be used according to the invention, in particular those as described herein as preferred, are suitable as odor modifiers, preferably (a) for masking or reducing the or one or more unpleasant olfactory impression(s) of one or more unpleasantly smelling substances, and/or (b) for enhancing the or one or more pleasant olfactory impression(s) of one or more pleasantly smelling substance(s), in particular in combination with (other) fragrance substances as described above.

Preferred is the use of the compounds to be used according to the invention in a composition, preferably a perfume oil, which contains one or more (further) pleasantly and/or unpleasantly smelling substances, the unpleasant olfactory impression of which is masked or reduced by the mixture according to the invention and/or the pleasant olfactory impression of which is enhanced by the mixture according to the invention, wherein this pleasantly and/or unpleasantly smelling substance, or one, more or all of these pleasantly and/or unpleasantly smelling substances is/are selected from the group consisting of alcohols, aldehydes, ketones, ethers, esters and carboxylates, preferably ketones and esters, and/or has/have a molar mass in the range from 150 to 285 g/mol.

Also described herein in this context is a process (a) for masking or reducing the or one or more unpleasant olfactory impression(s) of one or more unpleasantly smelling substances, and/or (b) for enhancing the or one or more pleasant olfactory impression(s) of one or more pleasantly smelling substance(s), comprising the following step:

Mixing the (a) pleasant and/or (b) unpleasant smelling substance(s) with a fragrance composition according to the invention or, preferably, a compound to be used according to the invention as defined herein, in a weight ratio as defined herein according to the invention, wherein the amount of the fragrance composition according to the invention or of the compound to be used according to the invention is sufficient to (a) enhance the pleasant olfactory impression(s) of the pleasantly smelling substance(s) and/or to (b) reduce or mask the unpleasant olfactory impression(s) of the unpleasantly smelling substance(s).

Another aspect of the present invention is a method for producing a perfumed product, in particular a perfumed product according to the invention (as described herein), comprising the following steps:

(i) providing a compound to be used according to the invention defined or a fragrance composition according to the invention, ii) providing one or more further components of the perfumed product to be prepared, and iii) contacting or mixing the further components provided in step ii) with a sensorially effective amount of the components provided in step i).

The synthesis of the compounds (A to D) to be used according to the invention can be carried out according to the following scheme:

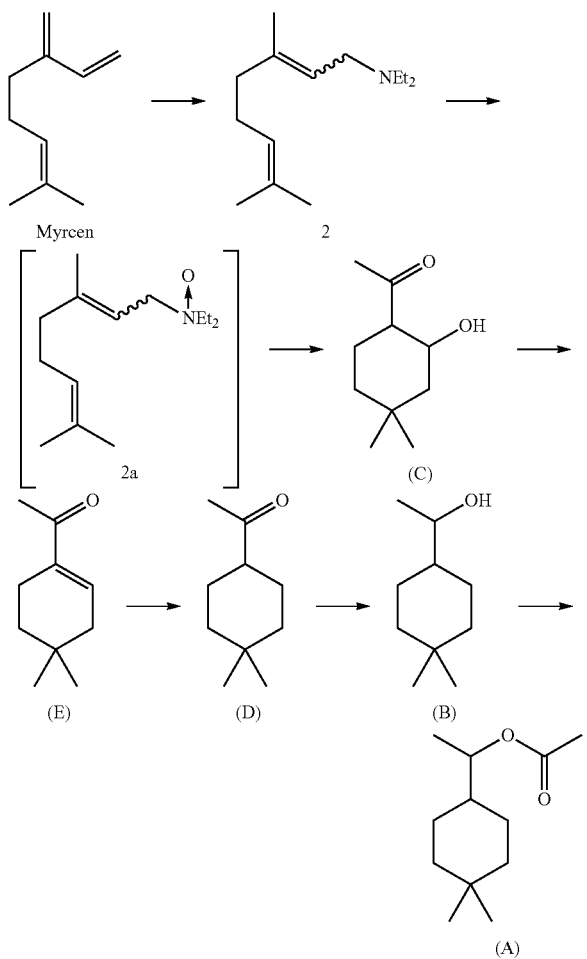

The synthesis steps starting from myrcene up to and including compound (D) is already described in the literature (Kunihiko Takabe et al. Cyclization of N,N-diethylgeranylamine N-oxide in one-pot operation: preparation of cyclic terpenoid-aroma chemicals, Tetrahedron Letters, Volume 49, Issue 41, 2008, pages 6016-6018), however, no odor characterization is described and compound (C) is only described theoretically without this compound being isolated and confirmed by analytical means.

Another aspect of the present invention is a method for preparing 1-(4,4-dimethylcyclohexyl)ethanol or 1-(4,4-dimethylcyclohexyl)ethyl acetate comprising the following reaction step:

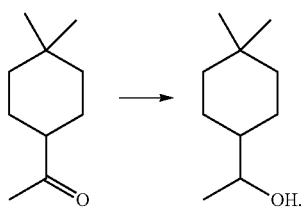

Preferably, the reduction of the ketone is carried out by a hydride, preferably lithium aluminum hydride, sodium borohydride or sodium hydride, particularly preferably sodium borohydride.

Preferred according to the invention is a process for the production of 1-(4,4-dimethylcyclohexyl)ethyl acetate, (additionally) comprising the following reaction step:

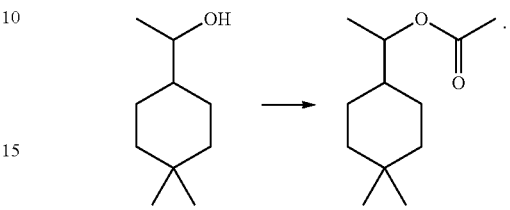

The acetylation is preferably carried out with acetyl chloride or acetic anhydride, preferably with acetyl chloride.

In the following, the present invention is illustrated in more detail by means of selected examples. Unless otherwise indicated, all data refer to weight.

EXAMPLE 1: PRODUCTION OF 1-(2-HYDROXY-4,4-DIMETHYL-CYCLOHEXYL) ETHANONE (C)

To a solution of N,N-diethylgeranylamine (10 g, 0.048 mol) in methanol (50 mL) was added a 31% aqueous hydrogen peroxide solution (15.8 mL) at room temperature. The mixture was stirred for 48 hours and then about 30 mg of $MnO_2$ was added to decompose the excess oxidant. The reactant mixture was filtered over Celite and post-rinsed with methanol. The filtrate was freed from methanol under reduced pressure. The crude N-oxide (2a) was obtained. To this colorless aqueous solution was added 50% $H_2SO_4$ aq. (v/v 9.8 mL) was added. The mixture changed color from colorless to pink while stirred at 100° C. for eight hours. After cooling the solution to 0° C., a mixture of NaOH (10 g) and ice (10 g) was added to the solution. After controlled neutralization, the mixture was extracted with MTBE (100 mL×3) and the combined organic phases were washed with water, dried over $Na_2SO_4$ and freed from the solvent. 7 g of 1-(2-hydroxy-4,4-dimethyl-cyclohexyl)ethanone (C) was obtained. The crude product can be used for the subsequent synthesis (Example 2) without further processing.

$^1$H NMR (400 MHz, $CDCl_3$) δ 4.01 (ddd, J=11.7, 9.8, 4.4 Hz, 1H), 2.29-2.22 (m, 1H), 2.20 (s, 3H), 1.91-1.83 (m, 1H), 1.71 (ddd, J=12.6, 4.5, 2.1 Hz, 1H), 1.49-1.39 (m, 2H), 1.32-1.01 (m, 2H), 0.97 (s, 3H), 0.92 (s, 3H).

$^{13}$C NMR (151 MHz, $CDCl_3$) δ 212.87, 67.62, 59.06, 46.33, 38.32, 32.75, 31.88, 29.21, 24.91, 24.36.

Odor description: flowery, green, minty.

EXAMPLE 2: SYNTHESIS OF 1-(4,4-DIMETHYLCYCLOHEXEN-1-YL)ETHANONE (E)

To a solution of 1-(2-hydroxy-4,4-dimethyl-cyclohexyl) ethanone (C) (2.9 g, 0.171 mol) in methanol (15 mL), NaOH pellets (340 mg) were slowly added and the mixture was heated at reflux for two hours. Then, the mixture was mixed with 10% aqueous hydrochloric acid solution and extracted with MTBE (30 mL×3). The organic phases were combined, washed with saturated $NaHCO_3$ solution and subsequently with water and dried over $Na_2SO_4$. The mixture was freed from solvent and then purified by Kugelrohr distillation (70° C., 0.44 mbar). 1-(4,4-dimethylcyclohexen-1-yl)ethanone (E) was obtained (2.1 g, 81%).

$^1$H NMR (600 MHz, CDCl$_3$) δ 6.83 (tt, J=3.9, 1.7 Hz, 1H), 2.29 (s, 3H), 2.26 (tq, J=6.5, 2.3, Hz, 2H), 2.04 (dt, J=4.7, 2.6, Hz, 2H), 1.40 (t, J=6.5 Hz, 2H), 0.92 (s, 6H).

$^{13}$C NMR (151 MHz, CDCl$_3$) δ 199.20, 140.10, 138.47, 40.06, 34.84, 28.41, 28.12, 28.12, 25.30, 20.83.

Odor description: fruity, banana-like, caraway.

EXAMPLE 3: SYNTHESIS OF 1-(4,4-DIMETHYLCYCLOHEXYL)ETHANONE (D)

A mixture of 1-(4,4-dimethylcyclohexen-1-yl)ethanone (E) (11.8 g, 0.77 mol), isopropanol (60 mL) and a catalytic amount of Ru/C 5 wt.-% (0.9 g) was placed in a sealed reactor and hydrogenation was carried out at 130° C. and 5 to 10 bar hydrogen for 6 to 7 hours. The reaction mixture was subsequently filtered off, freed from solvent, and distilled by Kugelrohr distillation (131° C., 0.3 bar). 9.1 g (76%) 1-(4,4-dimethylcyclohexyl)ethanone (D) was obtained.

$^1$H NMR (400 MHz, CDCl$_3$) δ 2.24 (tt, J=11.6, 3.8 Hz, 1H), 2.14 (s, 3H), 1.75-1.66 (m, 2H), 1.58-1.40 (m, 4H), 1.20 (td, J=13.1, 3.9 Hz, 2H), 0.92 (s, 3H), 0.89 (s, 3H).

$^{13}$C NMR (101 MHz, CDCl$_3$) δ 212.47, 51.41, 38.42, 38.43, 32.40, 29.80, 28.05, 24.44, 24.44, 24.35.

Odor description: spicy, savory, caraway.

EXAMPLE 4: SYNTHESIS OF 1-(4,4-DIMETHYLCYCLOHEXYL)ETHANOL (B)

To a cooled solution of 1-(4,4-dimethylcyclohexyl)ethanone (D) (7.0 g, 0.045 mol) in MeOH (13.5 mL) a mixture of NaBH$_4$ (0.7 g, 0.018 mol) in 1% NaOH solution (2.8 mL) was carefully added and then stirred for four hours at room temperature. Approximately half of the methanol was subsequently removed at the rotary evaporator and 100 mL of cooled water was added. The aqueous mixture was extracted with MTBE (50 mL×3). The combined organic phases were washed with water, dried over Na$_2$SO$_4$, and then freed from solvent at 60° C. and 500 to 10 mbar. 6 g of 1-(4,4-dimethylcyclohexyl)ethanol (B) was obtained as crude product. The crude product can be purified by column chromatography (cyclohexane:ethyl acetate 3:1). 5.8 (83%) 1-(4,4-dimethylcyclohexyl)ethanol (B) is obtained.

$^1$H NMR (600 MHz, Benzene-d$_6$) δ 3.31 (h, J=6.09 Hz, 1H), 1.65-1.57 (m, 1H), 1.39-1.30 (m, 3H), 1.16-1.05 (m, 4H), 0.99 (d, J=6.32 Hz, 3H), 0.98 (d, J=6.28 Hz, 1H), 0.90 (s, 3H), 0.84 (s, 3H), 0.69 (d, J=4.84 Hz, 1H, —OH).

$^{13}$C NMR (151 MHz, C$_6$D$_6$) δ 71.60, 45.38, 39.38, 39.28, 33.20, 24.97, 24.32, 24.33, 24.25, 20.94.

Odor description: flowery, blossoming, citrus, soft, plum, body lotion.

EXAMPLE 5: SYNTHESIS OF 1-(4,4-DIMETHYLCYCLOHEXYL)ETHYL ACETATE (A)

A mixture of 9.6 g (61.4 mmol) 1-(4,4-dimethylcyclohexyl)ethanol (B), cyclohexane (150 mL), and pyridine (7.4 mL) was placed under a nitrogen atmosphere and 6.3 g acetyl chloride was added dropwise at a temperature between 0 and 5° C. After the reaction was complete, 50 mL of water was added and the mixture was stirred for 15 minutes. The organic phase was separated and washed with 25% H$_2$SO$_4$ solution (25 mL×2), water (25 mL×2) and saturated NaHCO$_3$ solution. The organic phase was then dried over sodium sulfate, filtered and then freed from solvent at 60° C. and 500 to 10 mbar. 10.84 g (89%) of 1-(4,4-dimethylcyclohexyl)ethyl acetate (A) was obtained.

$^1$H NMR (400 MHz, CDCl$_3$) δ 4.75 (p, J=6.4 Hz, 1H), 2.03 (s, 3H), 1.56 (ddd, J=10.5, 7.1, 5.1 Hz, 1H), 1.49 (ddd, J=11.1, 5.7, 1.8 Hz, 1H), 1.45-1.35 (m, 1H), 1.38-1.30 (m, 1H), 1.27-1.19 (m, 2H), 1.18 (d, J=6.4 Hz, 3H), 1.16-1.08 (m, 3H), 0.89 (s, 3H), 0.86 (s, 3H). 13C NMR (101 MHz, CDCl$_3$) δ 170.84, 74.55, 42.55, 38.81, 38.76, 32.84, 29.98, 24.31, 24.31, 24.15, 21.33, 17.31.

Odor description: green, herbaflorate, violet, rose, flowery, powdery.

EXAMPLE 6: PERFUME EXAMPLES WITH ADDITION OF 1-(4,4-DIMETHYLCYCLOHEXYL)ETHYL ACETATE (A)

| | Reference example (not according to the invention) | Example according to the invention |
|---|---|---|
| AGRUMEX HC | 80 | 80 |
| ALDEHYDE C14 SOG | 50 | 50 |
| ALDEHYDE C16 SOG. | 1 | 1 |
| AMBROXIDE | 4 | 4 |
| ANISALDEHYDE PURE | 16 | 16 |
| APPLE GREEN AROMABASE | 15 | 15 |
| APRIFLOREN ® | 1 | 1 |
| BERGAMOT OIL | 20 | 20 |
| CITRONELLOL 950 | 40 | 40 |
| CITRONELLYL ACETATE EXTRA | 10 | 10 |
| 1-(4,4-dimethylcyclohexyl)ethyl acetate (A) | 0 | 20 |
| DECALACTONE GAMMA | 5 | 5 |
| DIHYDROMYRCENOL | 100 | 100 |
| DIPROPYLENE GLYCOL | 58 | 38 |
| ETHYLVANILLIN 10% DPG | 4 | 4 |
| EUGENOL NAT. | 3 | 3 |
| FRAMBINON ® 10% DPG | 6 | 6 |
| GERANYL ACETATE 60 | 20 | 20 |
| GERANYL TIGLATE | 5 | 5 |
| GLOBALIDE ® | 25 | 25 |
| HEDIONE | 60 | 60 |
| HEXENAL TRANS-2 10% DPG | 6 | 6 |
| HEXENYL ACETATE CIS-3 10% DPG | 9 | 9 |
| HEXYL ACETATE | 50 | 50 |
| HEXYLSALICYLATE | 15 | 15 |
| INDOFLOR ® CRYST. 10% DPG | 2 | 2 |
| ISO E SUPER | 20 | 20 |
| ISORALDEINE 70 | 15 | 15 |
| JASMIN 61 TYPE BASE | 20 | 20 |
| LINALOOL | 80 | 80 |
| LINALYL ACETATE | 150 | 150 |
| PHENIRAT ® | 50 | 50 |
| ROSE DE MAI-BASE | 30 | 30 |
| ROSE OXIDE L | 5 | 5 |
| SANDRANOL ® | 15 | 15 |
| VERTOCITRAL | 10 | 10 |
| | 1000 | 1000 |

Addition of 2% of 1-(4,4-dimethylcyclohexyl)ethyl acetate gives the perfume blend a more flowery, natural and softer fragrance.

EXAMPLE 7: COMBINATION OF 1-(4,4-DIMETHYLCYCLOHEXYL)ETHYL ACETATE WITH 1-(3,3-DIMETHYLCYCLOHEXYL)ETHYL ACETATE

Four mixtures of 1-(4,4-dimethylcyclohexyl)ethyl acetate with 1-(3,3-dimethylcyclohexyl)ethyl acetate were prepared according to the table below and the odor of each mixture was determined.

| No.: | Proportion of 1-(3,3-dimethyl-cyclohexyl)ethyl acetate | Dosage of 1-(4,4-dimethylcyclo-hexyl)ethyl acetate | Odor |
| --- | --- | --- | --- |
| 1 | 100 parts by weight | without addition | fruity-apple-pear-like, sweet, flowery-woody |
| 2 | 100 parts by weight | with 1 wt.-% addition | the mixture becomes more flowery, softer and more natural |
| 3 | 100 parts by weight | with 2 wt.-% addition | the mixture gets a slight musk-ambergris odor |
| 4 | 100 parts by weight | with 4 wt.-% addition | the effects become distinctly stronger than for the 2% addition |
| 5 | 100 parts by weight | with 8 wt.-% addition | the mixture becomes more spicy |

Addition of 1-(4,4-dimethylcyclohexyl)ethyl acetate to 1-(3,3-dimethylcyclohexyl)ethyl acetate significantly improved the fragrance profile. The addition of 2-4 wt.-% of 1-(4,4-dimethylcyclohexyl)ethyl acetate was found to be of particular interest.

EXAMPLE 8: ALCOHOLS FROM THE DIHYDROMYRCENOL PROCESS

In the table below, products of the dihydromyrcenol process are represented. The structures, the proportions determined by GC and the odor description of the respective compound are given in the table:

| | Structure | % | Odor |
| --- | --- | --- | --- |
| 1 | [structure] | 66-75 | terpineol-like, animalistic camphor |
| 2 | [structure] | 2-5 | flowery citric, fruity plum |
| 3 | [structure] | 12-22 | slightly musty, camphor-like, animalistic |
| 4 | [structure] | 0.5-4 | musty-earthy, camphor-like, fresh |
| 5 | [structure] | 0.4-4 | slightly musty, camphor-like, minty |
| 6 | [structure] | 0.1-2 | musty-earthy, terpineol-like |

EXAMPLE 9: ACTATES FROM THE DIHYDROMYRCENOL PROCESS

The compounds of the alcohol mixture from Example 8 were converted into the respective ethyl acetate analogously to the synthesis procedure from Example 5. In the table below, products of the acetylation are shown. The structures, the proportions determined by GC and the odor description of the respective compound are given in the table:

| | Structure | % | Odor |
| --- | --- | --- | --- |
| 1 | [structure] | 66-75 | fruity-apple-pear-like, sweet, flowery-woody |
| 2 | [structure] | 2-5 | green, herbaflorate, violet, rose, flowery, powdery |
| 3 | [structure] | 13-22 | green, root-like, flowery |

| | Structure | % | Odor |
|---|---|---|---|
| 4 | H₃C, CH₃ cycloheptane with H₃C and OAc | 0.5-4 | woody-flowery |
| 5 | H₃C, CH₃ cyclohexane with OAc and CH₃ | 0.4-4 | flowery, green, woody |
| 6 | H₃C, CH₃ cycloheptane with CH₃ and OAc | 0.1-2 | woody-flowery, slightly root-like |

The invention claimed is:

1. A method for imparting a flowery and/or fruity olfactory characteristic to a composition comprising adding a compound selected from the group consisting of 1-(4,4-dimethylcyclohexyl)ethanone, 1-(4,4-dimethylcyclohex-1-en-1-yl)ethanone, 1-(4,4-dimethylcyclohexyl)ethanol, 1-(4,4-dimethylcyclohexyl)ethyl acetate, and 1-(2-hydroxy-4,4-dimethylcyclohexyl)ethanone to the composition in an amount sufficient to impart a flowery and/or fruity olfactory characteristic to the composition.

2. The method according to claim 1, wherein the compound is 1-(4,4-dimethylcyclohexyl)ethyl acetate.

3. The method according to claim 1, wherein the compound is 1-(4,4-dimethylcyclohexyl)ethanol.

4. The method according to claim 1, wherein the compound is 1-(2-hydroxy-4,4-dimethylcyclohexyl)ethanone.

5. A fragrance composition comprising a compound selected from 1-(4,4-dimethylcyclohexyl)ethanone, 1-(4,4-dimethylcyclohex-1-en-1-yl)ethanone, 1-(4,4-dimethylcyclohexyl)ethanol, 1-(4,4-dimethylcyclohexyl)ethyl acetate, and 1-(2-hydroxy-4,4-dimethylcyclohexyl)ethenone, wherein the compound is in an amount sufficient to impart a flowery and/or fruity olfactory characteristic to the fragrance composition.

6. The fragrance composition according to claim 5, additionally comprising one or more further fragrance substance(s).

7. The fragrance composition according to claim 5, additionally comprising 1-(3,3-dimethylcyclohexyl)ethyl acetate.

8. The fragrance composition according to claim 7, wherein the molar ratio between the compound and 1-(3,3-dimethylcyclohexyl)ethyl acetate is 1:199 to 1:4.

9. The fragrance composition according to claim 7, wherein the molar ratio between the compound and 1-(3,3-dimethylcyclohexyl)ethyl acetate is 1:199 to 1:9.

10. The fragrance composition according to claim 7, wherein the molar ratio between the compound and 1-(3,3-dimethylcyclohexyl)ethyl acetate is 2:99 to 1:19.

11. The fragrance composition according to claim 7, wherein the molar ratio between the compound and 1-(3,3-dimethylcyclohexyl)ethyl acetate is 1:49 to 1:24.

12. The fragrance composition according to claim 5, wherein the compound is 1-(4,4-dimethylcyclohexyl)ethyl acetate.

13. A perfumed product comprising the fragrance composition according to claim 5.

14. The perfumed product according to claim 13, wherein the product is selected from the group consisting of perfume extracts, eau de parfums, eau de toilettes, aftershaves, eau de colognes, pre-shave products, splash colognes, perfumed refreshing tissues, acid, alkaline and neutral detergents, fabric refreshers, ironing aids, liquid detergents, powder detergents, laundry pre-treatment products, fabric softeners, laundry soaps, laundry tablets, disinfectants, surface disinfectants, air refreshers, aerosol sprays, waxes and polishes, personal care products, hand creams and lotions, foot creams and lotions, depilatory creams and lotions, after-shave creams and lotions, tanning creams and lotions, hair care products, deodorants and antiperspirants, products of decorative cosmetics, candles, lamp oils, incense sticks, insecticides, repellents, and propellants.

15. A method for producing a perfumed product according to claim 13 comprising:
(i) providing a compound selected from 1-(4,4-dimethylcyclohexyl)ethanone, 1-(4,4-dimethylcyclohex-1-en-1-yl)ethanone, 1-(4,4-dimethylcyclohexyl)ethanol, 1-(4,4-dimethylcyclohexyl)ethyl acetate, and 1-(2-hydroxy-4,4-dimethylcyclohexyl)ethanone,
ii) providing one or more further components of the perfumed product to be produced, and
iii) contacting or mixing the one or more further components with a sensorially effective amount of the compound of (i).

16. A method for producing 1-(4,4-dimethylcyclohexyl)ethanol or 1-(4,4-dimethylcyclohexyl)ethyl acetate comprising the following reaction step:

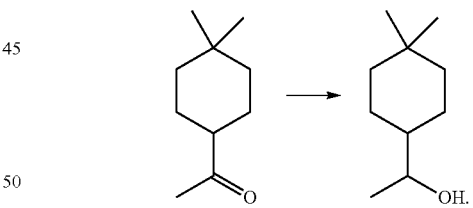

17. A method for imparting a flowery and/or fruity olfactory characteristic to a composition comprising adding 1-(4,4-dimethylcyclohexyl)ethyl acetate to the composition in an amount sufficient to impart the flowery and/or fruity olfactory characteristic to the composition.

18. A perfumed product comprising the fragrance composition of claim 7, wherein the compound is 1-(4,4-dimethylcyclohexyl)ethyl acetate.

19. The perfumed product according to claim 18, wherein the product is selected from the group consisting of perfume extracts, eau de parfums, eau de toilettes, aftershaves, eau de colognes, pre-shave products, splash colognes, perfumed refreshing tissues, acid, alkaline and neutral detergents, fabric refreshers, ironing aids, liquid detergents, powder detergents, laundry pre-treatment products, fabric softeners, laundry soaps, laundry tablets, disinfectants, surface disinfectants, air refreshers, aerosol sprays, waxes and polishes, personal care products, hand creams and lotions, foot creams and lotions, depilatory creams and lotions, after-shave creams and lotions, tanning creams and lotions, hair care products, deodorants and antiperspirants, products of decorative cosmetics, candles, lamp oils, incense sticks, insecticides, repellents, and propellants.

\* \* \* \* \*